(12) United States Patent
Guardia

(10) Patent No.: US 9,370,411 B2
(45) Date of Patent: Jun. 21, 2016

(54) EXTERNAL MALE INCONTINENCE DEVICE

(71) Applicant: Remo Guardia, Oshawa (CA)

(72) Inventor: Remo Guardia, Oshawa (CA)

(*) Notice: Subject to any disclaimer, the term of this patent is extended or adjusted under 35 U.S.C. 154(b) by 89 days.

(21) Appl. No.: 14/465,852

(22) Filed: Aug. 22, 2014

(65) Prior Publication Data

US 2015/0059777 A1 Mar. 5, 2015

(30) Foreign Application Priority Data

Aug. 28, 2013 (CA) ...................................... 2824958

(51) Int. Cl.
*A61F 5/48* (2006.01)
*A61F 2/00* (2006.01)
*A61B 17/122* (2006.01)
*A61F 2/08* (2006.01)

(52) U.S. Cl.
CPC ............ *A61F 2/0054* (2013.01); *A61B 17/1227* (2013.01); *A61F 5/48* (2013.01); *A61F 2/08* (2013.01); *A61F 2240/001* (2013.01); *Y10T 29/4987* (2015.01)

(58) Field of Classification Search
CPC ...... A61F 2/0054; A61F 5/48; A61B 17/1227
See application file for complete search history.

(56) References Cited

U.S. PATENT DOCUMENTS

| | | | | | |
|---|---|---|---|---|---|
| 3,511,230 | A | * | 5/1970 | Strong | A61F 5/41 600/41 |
| 3,920,007 | A | * | 11/1975 | Line | A61F 5/41 52/717.03 |
| 4,203,432 | A | * | 5/1980 | Koch | A61F 5/41 600/41 |
| 4,262,663 | A | * | 4/1981 | Allinson | A61F 5/41 600/39 |
| 4,785,802 | A | * | 11/1988 | Blount | A61F 5/41 600/39 |
| 4,971,074 | A | * | 11/1990 | Hrubetz | A61F 5/48 128/885 |
| 5,336,157 | A | * | 8/1994 | Hale | A61B 17/1227 128/843 |
| 7,544,161 | B1 | * | 6/2009 | Wooten, Sr. | A61F 5/41 600/38 |
| 7,690,220 | B2 | * | 4/2010 | Okamura | A44C 15/005 446/129 |

* cited by examiner

*Primary Examiner* — Kristen Matter

(57) ABSTRACT

This invention provides a male incontinence device for external use. The device has a soft elongated body that has at least one flexible wire centrally positioned in the body. The body is bendable to form a U-shape comprising first and second arms extending from a U-bend, each of the first and second arms comprising a gripping portion disposed between the U-bend and a distal end of the arm. The device further has at least one elastic band for holding the arms in a desired position.

12 Claims, 2 Drawing Sheets ically 1 mm/18 GA to 2.5 mm/12 GA.

EXTERNAL MALE INCONTINENCE DEVICE

FIELD

This invention relates to male incontinence devices. In particular, this invention relates to male incontinence devices for external use.

BACKGROUND

After a radical prostatectomy surgery, radiotherapy, or because of other conditions like old age, a man's sphincter or urethra, or both, may suffer damage and a leakage (dribbling) of urine may occur.

Incontinence items and devices exist on the market, for example diapers, pads, clamps. However, all are far from being totally effective and problem free. The devices or clamps available today are very expensive, uncomfortable and painful if they are worn for hours: they pinch the penis skin of the user, for example when driving a car, and they often apply too much pressure on the urethra. Further, pieces of some devices will sometimes fall in toilet bowls as the user urinates.

BRIEF DESCRIPTION OF THE DRAWINGS

In drawings which illustrate embodiments by way of example only.

DETAILED DESCRIPTION

In an implementation, a male incontinence device is provided. The device comprises a soft elongated body having at least one flexible galvanized wire centrally positioned therein; the body bendable to form a U-shape comprising first and second arms extending from a U-bend, each of the first and second arms comprising a gripping portion disposed between the U-bend and a distal end of the arm; and at least one rubber or elastic band for holding the arms in a desired position.

In another implementation, a method of manufacturing an external male incontinence device is provided. The method comprises the steps of positioning at least one flexible wire lengthwise in a soft elongated body; bending the body to form a U-shape comprising first and second arms extending from a U-bend, each of the first and second arms comprising a gripping portion disposed between the U-bend and a distal end of the arm; and providing at least one elastic band to be wrapped around the arms.

In another implementation, a method of assembling a male incontinence device for use is provided. The method comprises the steps of bending a soft elongated body having at least one flexible wire positioned centrally therein to form a U-shape comprising first and second arms extending from a U-bend, each of the first and second arms comprising a gripping portion disposed between the U-bend and a distal end of the arm; placing the gripping portions of the first arm and second arm on opposing sides of a user's penis; and wrapping at least one elastic band around the arms.

Figure 1:
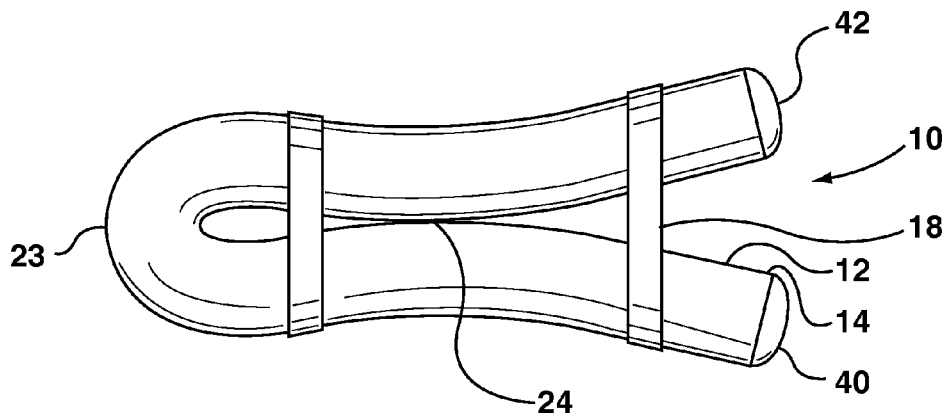
FIG. 1 is a top side view of a male incontinence device.
Figure 2:
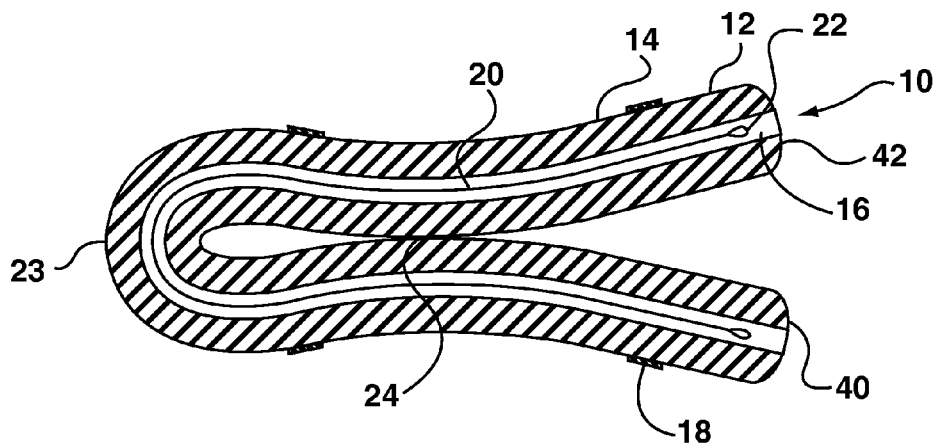
FIG. 2 is a cross-sectional view of the male incontinence device of FIG. 1.

Referring to FIGS. 1 and 2, a male incontinence device 10 is illustrated. The device 10 comprises an elongated body 12 having a waterproof surface 14 and central hollow cavity 16. The body 12 may be fabricated from foam, silicone, or soft rubber, or any similar soft, waterproof, and safe materials known in the art. The body 12 may be any suitable shape, for example cylindrical, or rectangular. As shown in FIG. 2, the device 10 further comprises one or more flexible galvanized wires 20 for inserting into the body 12.

Figure 3:
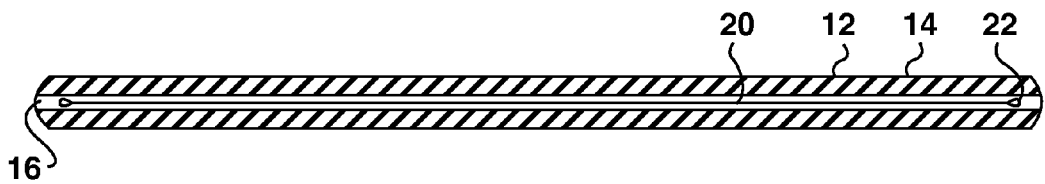
FIG. 3 is a cross-sectional view of a body of the invention having one wire therein.

Referring to FIGS. 2 and 3, an embodiment of the invention comprising one wire 20 is illustrated. The thickness of the wire 20 that is inserted into the cavity 16 of the body 12 is 1.3 mm/16 GA to 2.5 mm/12 GA. Preferably, before inserting the wire 20, approximately 4 to 9 millimeters of the wire 20 is bent (the folding length is determined by the flexibility of the wire 20) inward at each end. Once inserted into the body 12, the gap between the wire 20 and each end of the body 12 will be filled, for example with glue.

Figure 7:
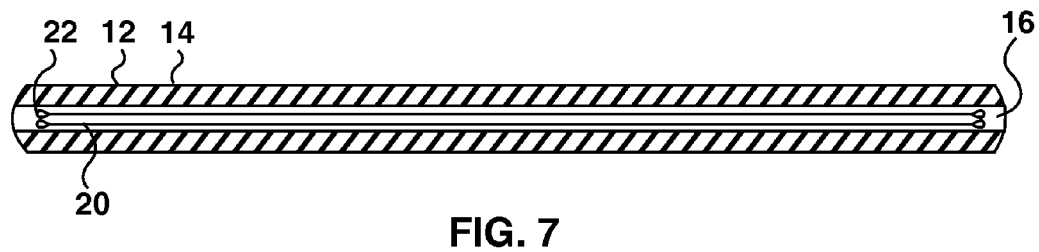
FIG. 7 is a cross-sectional view of a body of the invention having two wires therein.

Referring to FIG. 7, the body 12 of an embodiment of the invention having two wires 20 therein is illustrated. The thickness of each wire 20 may be the same or different from the other wire 20 inside the body 12.

Figure 5:
FIG. 5 is a perspective view of a body of the invention wherein the body's hollow cavity is filled with glue.

The procedure for two and three wires 20 is the same as that for a one wire device 20. Before inserting the wires 20 into the cavity 16 of the body 12, approximately 4 to 9 millimeters of each wire's end 22 will be folded for safety reasons, and then, after the wires 20 are in place, the gaps between the wires 20 and the end of the cavity 16 will be filled with glue 30, so that rust and bacteria does not enter or come out of the cavity 16, as shown in FIG. 5. The use of glue 30 prevents infections.

The thickness of each wire 20 may be approximately 1 mm/18 GA if three wires 20 are used, 1.3 mms/16 GA if two or three wires 20 are used, and 1.63 mms/14 GA if two or three wires are used. Preferably, GA20 wires is used for a device 10 having three or four wires 20.

Figure 4:
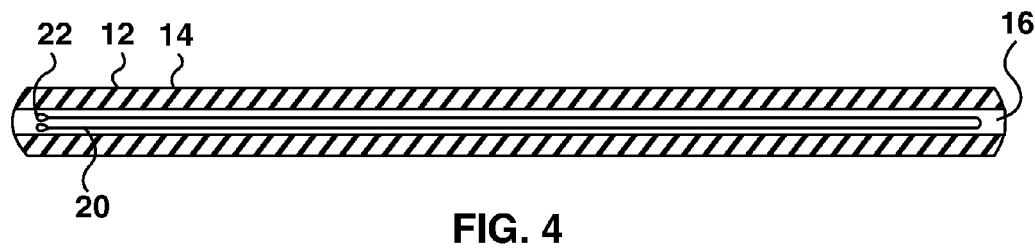
FIG. 4 is a cross-sectional view of a body of the invention having one wire folded in half therein.

In an embodiment of the invention comprising two wires 20, preferably a wire 20 that has a little more than twice the length of the body 12 is used and folded once, as shown in FIG. 4. For embodiments of the invention comprising three and four wires 20, the wire 20 is folded twice and three times respectively.

For example, if the device 10 requires an 18 centimeter wire 20, a 36 centimeter wire 20 is selected and then, it is folded in half for a device 10 having two wires 20. If the device has three wires 20 the wire 20 will be 54 centimeters and folded twice. As described above, at least one millimeter of the cavity 16 is needed on each side of the body 12 for glue 30 and 4 to 9 millimeters (less for smaller wires 20) of the wires 20 are required to be folded at the end of each side as well. The wire 20 should be cut to fit the body 12. For the embodiments having three or four wires 20, the wire 20 is folded twice and three times respectively and the procedure for two wires 20 is followed.

Figure 6:
FIG. 6 is a side view of the body of FIG. 5 having caps on the ends of the body.

In the body 12 shown in FIG. 6, each side of the device 10 is smeared with glue 30, for example super glue or waterproof glue, and a cap 32, for example a circular piece of impermeable foam or rubber or other suitable material is attached to each end of the body 12. The cap 32 may be omitted or reduced in size if the ends of the body 12 are waterproofed and the wires 20 secured.

Preferably, the thickness of the body 12 is approximately 8 mm to 1.8 cms in diameter. The wire 20 thickness is preferably approximately 1 mm to 2.5 mm (GA 18 to GA 12). However, other thicknesses of the body 12, such as 4 mm and 6 mm, for the foam, and wires 20 thickness in diameter, may also achieve similar results and may be used. Persons skilled in the art will appreciate that penis size varies from user to user. Consequently, various sizes and length of wires 20 and bodies 12 may be used to suit a particular user's needs.

The extended average device's 10 length is about 16 cms to 24 cm long. When the device 10 is folded its length is approximately 8 centimeters to 12 long. The device 10 may also be offered custom made to fit men with larger characteristics.

Referring to FIG. 1, the device 10 further comprises at least one rubber or elastic band 18 with a diameter of about 1 cm, to 5 cm, before extension, and is at least 1 mm wide (1-4 mm etc.). The band 18 completes the device 10 when it is placed on one side of it. Two bands 18 may be used, one on each side of the device 10, as shown in FIG. 1. The size of the band 18 may change according to the size of the man's penis and the thickness of the body 12.

The device 10 may be assembled by inserting one or more wires 20 into the body 12 via the cavity 16, filling in with glue 30 the cavity 16, smearing each end of the body 12 with super glue and sealing the ends of the body 12 with a round waterproof cap 32 (foam or rubber), and folding the device 10 in half, as shown in FIG. 1. Alternatively, the body 12 could be fabricated with one or more wires 20 centrally embedded therein.

In use, when the device 10 is folded in half, it takes the approximate shape of a letter "U", and it forms an U-bend 23 where the body 12 is folded and a first arm 40 and second arm 42 that are generally parallel. The centre of the arms 40 and 42 are pinched together to form an arch 24, shown in FIGS. 1 and 2.

Having folded the device 10 in half, the user will put the center of the first arm 40 at the arch 24 under the urethra and the second arm 42 on the penis's top before the corona's head, leaving a space on distal ends of the arms 40 and 42 (not shown). The arch 24 allows for two spaces on either side the penis, which allows blood circulation. The user will then wrap a first band 18 around the distal ends of the arms 40 and 42 and, optionally, wrap a second band 18 around the arms 40 and 42 adjacent the U-bend 23. The bands 18 squeeze the arms 40 and 42 and generates pressure to reduce or stop the leakage of urine from the penis. The user may adjust the device 10 to ensure that the first arm 40 presses the urethra and may adjust the device 10 to comfort (not shown). The device 10 will function without an arch 24 as long as the distal ends of the arms 40 and 42 are bent away from each other.

As long as the urethra is pressed, the device 10 will still work if the user places it on any part of the penis shaft. The body 12, squeezed by the bands 18 and wires 20, applies pressure on the urethra, reducing the flow of urine. In another embodiment of the invention, a longer device 10 may be used and placed before the user's scrotum and on the top of the penis shaft, making the device 10 less conspicuous. This device 10 may also stimulate and allows intimacy. The device 10 reduces the flow of urine, lessening the discomfort and pain that usually is present when one wears clamps or other devices.

The present invention stops or immensely reduces the leakage of urine and reduces harm to the penis, as compared to prior art devices, because the wires 20 will bend when there is too much pressure on them. This device 10 is small, inexpensive and adjustable and can be used in hospitals, intensive care clinics, retirement centers etc., and may replace diapers. It minimizes pain on the urethra or on the penis.

Various embodiments of the present invention having been thus described in detail by way of example, it will be apparent to those skilled in the art that variations and modifications may be made without departing from the invention. The invention includes all such variations and modifications as fall within the scope of the appended claims.

The invention claimed is:

1. A male incontinence device for external use, comprising:
   a soft elongated body having at least one flexible wire centrally positioned therein; the body bendable to form a U-shape comprising first and second arms extending from a U-bend, each of the first and second arms comprising a gripping portion disposed between the U-bend and a distal end of the arm; and
   at least one elastic band for holding the arms in a desired position; wherein ends of the at least one flexible wire are folded over and wherein a gap is defined between each folded end of the at least one flexible wire and a corresponding distal end of the first or second arm, the gap sealed by glue deposited therein.

2. The device of claim 1 wherein the gripping portions of the first arm and second arm comprise corresponding arcuate portions that bring the arms closer together at a point along the corresponding arcuate portions.

3. The device of claim 1 wherein the at least one elastic band comprises a first elastic band for holding the first and second arms together at the distal end of the arms.

4. The device of claim 3 wherein the at least one elastic band further comprises a second elastic hand for holding the arms together adjacent to the U-bend.

5. The device of claim 1 wherein the ends of the at least one flexible wire are sealed by a cap fixed over each distal end.

6. The device of claim 1 wherein the body has a waterproof surface.

7. The device of claim 1 wherein the body is made of either foam or rubber.

8. The device of claim 1 wherein the body has a diameter of about 0.4 cm to about 1.8 cm and a length of about 16 cm to about 24 cm.

9. The device of claim 1 wherein the at least one flexible wire has a thickness of about 1 mm to about 2.5 mm.

10. The device of claim 1 wherein the at east one flexible wire has a gauge of 18 to 12.

11. The device of claim 1, wherein the at least one flexible wire comprises: three wires having a thickness of about 1 mm and a gauge of about 18;
   two or three wires having a thickness of about 1.3 mm and a gauge of about 16; two or three wires having a thickness of about 1.63 mm and a gauge of about 14; or, three or four wires having a gauge of about 20.

12. The device of claim 1 wherein the at least one elastic band has a diameter of about 1 cm to about 5 cm and a width of at least 1 mm before extension.

* * * * *